(12) United States Patent
Giridharagopalan et al.

(10) Patent No.: US 11,045,348 B2
(45) Date of Patent: Jun. 29, 2021

(54) APPARATUS FOR MANDIBULAR ADVANCEMENT OF AN ORAL APPLIANCE

(71) Applicant: Archis Health Investments LLC, Eden Prairie, MN (US)

(72) Inventors: Subhalakshmi Giridharagopalan, Eden Prairie, MN (US); Jayant Parthasarathy, Eden Prairie, MN (US)

(73) Assignee: Archis Health Investments LLC, Excelsior, MN (US)

( * ) Notice: Subject to any disclaimer, the term of this patent is extended or adjusted under 35 U.S.C. 154(b) by 120 days.

(21) Appl. No.: 16/405,934

(22) Filed: May 7, 2019

(65) Prior Publication Data

US 2019/0343675 A1 Nov. 14, 2019

Related U.S. Application Data

(60) Provisional application No. 62/668,307, filed on May 8, 2018.

(51) Int. Cl.
*A61F 5/00* (2006.01)
*A61F 5/56* (2006.01)
(Continued)

(52) U.S. Cl.
CPC ............ *A61F 5/566* (2013.01); *A61B 5/4818* (2013.01); *A61B 13/00* (2013.01); *A61C 7/00* (2013.01);
(Continued)

(58) Field of Classification Search
CPC ...... A61F 5/566; A61F 2005/563; A61F 5/56; A61F 5/58; A61B 5/4818; A61B 13/00;
(Continued)

(56) References Cited

U.S. PATENT DOCUMENTS 4,472,138 A 9/1984 Howe
4,505,672 A 3/1985 Kurz
(Continued)

FOREIGN PATENT DOCUMENTS

DE 479035 6/1929
DE 29514984 10/1996
(Continued)

OTHER PUBLICATIONS

Thang, Nguyen Duc. 1700 Animated Mechanical Mechanisms: Part 1 Transmission of Continuous Rotation, Dec. 31, 2014, https://cpb-us-w2.wpmucdn.com/sites.gatech.edu/dist/2/334/files/2017/09/1700-Animated-Linkages.pdf) (Year: 2014).*
(Continued)

*Primary Examiner* — Alireza Nia
*Assistant Examiner* — Michael Milo
(74) *Attorney, Agent, or Firm* — Neustel Law Offices

(57) ABSTRACT

An apparatus for mandibular advancement of an oral appliance for use in the treatment of sleep apnea, snoring, and other conditions. The apparatus for mandibular advancement of an oral appliance generally includes a first appliance portion comprising a gear assembly having a drive gear, wherein rotation of the drive gear linearly displaces links. The appliance also has a second appliance portion with a link-engaging members, wherein the links exert a force on the link-engaging members when they are linearly displaced, and wherein the force causes the second appliance portion to be displaced relative to the first appliance portion.

17 Claims, 18 Drawing Sheets

(51) Int. Cl.
*A61C 7/08* (2006.01)
*A61C 8/00* (2006.01)
*A61C 7/36* (2006.01)
*A61C 7/00* (2006.01)
*A61F 5/58* (2006.01)
*A61B 5/00* (2006.01)
*A61C 11/00* (2006.01)
*A61B 13/00* (2006.01)

(52) U.S. Cl.
CPC .................. *A61C 7/08* (2013.01); *A61C 7/36* (2013.01); *A61C 8/00* (2013.01); *A61C 11/00* (2013.01); *A61F 5/56* (2013.01); *A61F 5/58* (2013.01); *A61F 2005/563* (2013.01)

(58) Field of Classification Search
CPC .. A61C 7/00; A61C 8/00; A61C 11/00; A61C 7/08; A61C 7/36
USPC ............................ 128/848, 860, 861; 607/42
See application file for complete search history.

(56) References Cited

U.S. PATENT DOCUMENTS

| | | | |
|---|---|---|---|
| 4,917,701 A | | 4/1990 | Morgan |
| 5,003,994 A | | 4/1991 | Cook |
| 5,324,196 A | | 6/1994 | Magill |
| 5,443,384 A | | 8/1995 | Franseen |
| 5,683,244 A | | 11/1997 | Truax |
| 5,823,193 A | | 10/1998 | Singer |
| 5,829,441 A | | 11/1998 | Kidd |
| 5,829,970 A | * | 11/1998 | Yousefian ................ A61C 7/00 433/7 |
| 5,848,891 A | | 12/1998 | Eckhart |
| 5,884,628 A | | 3/1999 | Hilsen |
| 5,921,942 A | | 7/1999 | Remmers |
| 6,055,986 A | | 5/2000 | Meade |
| 6,604,527 B1 | * | 8/2003 | Palmisano .............. A61F 5/566 128/848 |
| 6,729,335 B1 | | 5/2004 | Halstrom |
| 7,832,402 B2 | * | 11/2010 | Nelissen ................ A61F 5/566 128/848 |
| 8,215,312 B2 | * | 7/2012 | Garabadian et al. ... A61F 5/566 128/848 |
| 8,312,884 B2 | * | 11/2012 | Fuselier .................. A61F 5/566 128/848 |
| 8,534,289 B2 | * | 9/2013 | Hernandez .............. A61F 5/566 128/848 |
| 9,611,125 B2 | * | 4/2017 | Hiebenthal ........ B65H 75/4452 |
| 9,642,662 B2 | * | 5/2017 | Appenzeller ........ A61B 17/869 |
| 10,575,981 B2 | * | 3/2020 | Rayek et al. ............. A61C 7/08 |
| 2005/0028826 A1 | | 2/2005 | Palmisano |
| 2007/0235037 A1 | | 10/2007 | Thornton |
| 2010/0154802 A1 | * | 6/2010 | Fuselier .................. A61F 5/566 128/848 |
| 2013/0112210 A1 | * | 5/2013 | Stein ....................... A61F 5/566 128/848 |
| 2013/0140289 A1 | | 6/2013 | Baratier |
| 2014/0134561 A1 | | 5/2014 | Smith |
| 2016/0324681 A1 | * | 5/2016 | Flanagan ................ A61B 5/08 |
| 2017/0035534 A1 | * | 2/2017 | Ross ....................... A61F 5/566 |
| 2017/0196727 A1 | | 7/2017 | Giridharagopalan |
| 2018/0125701 A1 | * | 5/2018 | Hadas .................. A61B 5/4818 |

FOREIGN PATENT DOCUMENTS

| | | | | |
|---|---|---|---|---|
| FR | 2722973 | | 2/1996 | |
| SU | 1438759 | | 11/1988 | |
| SU | 1680139 | | 1/1989 | |
| WO | WO 95/08969 | | 4/1995 | |
| WO | WO 20071014429 | | 2/2007 | |
| WO | WO 2013/049751 | | 4/2013 | |
| WO | WO 2013/102095 | | 7/2013 | |
| WO | WO 2013/188660 | | 12/2013 | |
| WO | WO-2015187949 A1 | * | 12/2015 | ......... A61B 5/02055 |
| WO | WO-2017090062 A1 | * | 6/2017 | ............. A61C 7/125 |

OTHER PUBLICATIONS https://www.knowltondental.com/service-view/tap-appliances/; TAP Appliances from Knowlton Dental Associates Webpage; Sep. 2018.
https://www.resmed.com/us/en/healthcare-professional/products/narval-campaign.html; Narval Mouth Piece from ResMed Webpage; Sep. 2018.
https://www.snorelab.com/shop-snorerx/; SnoreRx Mouth Piece from SnoreLab Webpage; Sep. 2018.
http://www.respiremedical.com/respire-blue-plus; Respire Blue Mouth Piece from Respire Medical Webpage; Sep. 2018.
https://somnomed.com/en/dentists/somnodent/somnodent-flex/; SomnoDent Flex Mouth Piece from SomnoMed Webpage; Sep. 2018.

* cited by examiner

APPARATUS FOR MANDIBULAR ADVANCEMENT OF AN ORAL APPLIANCE

CROSS REFERENCE TO RELATED APPLICATIONS

I hereby claim benefit under Title 35, United States Code, Section 119(e) of U.S. provisional patent application Ser. No. 62/668,307 filed May 8, 2018. The 62/668,307 application is hereby incorporated by reference into this application.

STATEMENT REGARDING FEDERALLY SPONSORED RESEARCH OR DEVELOPMENT

Not applicable to this application.

BACKGROUND

Field

Example embodiments in general relate to an apparatus for mandibular advancement of an oral appliance for use in the treatment of snoring, sleep apnea, and other related disorders.

Related Art

Any discussion of the related art throughout the specification should in no way be considered as an admission that such related art is widely known or forms part of common general knowledge in the field.

During sleep the muscles of the airway become relaxed. The relaxation of these muscles in turn reduces the diameter of the airway. Typically, the airway of a person with sleep related breathing disorders is already restricted or reduced in size, and this natural relaxation reduces the airway further. The most common sleeping disorder is obstructive sleep apnea (OSA), which is characterized by recurring collapse of the upper airway during sleep, resulting in sleep fragmentation and oxygen desaturation. Oral appliances have emerged as an alternative to CPAP for OSA treatment. Oral appliances are designed to improve upper airway configuration and prevent collapse through alteration of jaw and tongue position. The most common mechanism of action is to hold the lower jaw in a more anterior position. These appliances are variously termed "mandibular advancement devices (MAD),"

Oral appliances, such as mouth guards, have been used for a number of years in in the treatment of snoring, sleep apnea, and other related disorders. An amount of advancement of the lower portion, if at all, relative to the upper portion, is fixed, and creates the positional relationship between the maxilla and mandible of a wearer. The position of the wearer's mandible, however, may sometimes need to be varied depending on conditions that may also vary from one night or time period to the next, such as the wearer's degree of fatigue, alcohol use, etc. Appliances that allow for bilateral adjusting mechanisms are the most comfortable for patients, but they typically require two screws to be equally adjusted.

SUMMARY

In example embodiments, the present apparatus permits control of a dorsal mandibular advancement in an oral appliance using a single screw or drive point, in contrast with current devices that require two adjusting points. Thus, an example embodiment is directed to an apparatus for mandibular advancement of an oral appliance. The apparatus for mandibular advancement of an oral appliance includes an adjustable oral appliance, comprising a first appliance portion comprising a gear assembly having a drive gear, wherein rotation of the drive gear rotates a helical member that extends from a front position to a rear position of the first appliance portion. A fixed nut is secured proximate the rear position of the first appliance portion. The appliance also has an actuator screw with a first end threadably engaged in the fixed nut and a second end rotatably coupled to the helical member.

A first link, such as a first flange, is slidably coupled to the first appliance portion, the first flange also being coupled to the actuator screw proximate the second end so that rotation of the actuator screw causes a linear displacement of the first flange as the actuator screw rotates within the fixed nut. A second appliance portion has a first link-engaging member, wherein the first flange exerts a force on the first link-engaging member when it is linearly displaced, and wherein the force causes the second appliance portion to be displaced relative to the first appliance portion.

In some example embodiments, the drive gear comprises a worm wheel. Further, the first appliance portion may comprise a maxillary portion and the second appliance portion may comprise a mandibular portion. Alternatively, the first appliance portion may comprise a mandibular portion and the second appliance portion may comprise a maxillary portion.

In an example embodiment, the appliance can include a second helical member that extends from a front position to a rear position of the first appliance portion, a second fixed nut secured proximate the rear position of the first appliance portion, and a second actuator screw having a first end threadably engaged in the second fixed nut and a second end rotatably coupled to the second helical member. In the embodiment, a second flange is slidably coupled to the first appliance portion, the second flange also being coupled to the second actuator screw proximate the second end so that rotation of the second actuator screw causes a linear displacement of the second flange as the second actuator screw rotates within the second fixed nut.

The embodiment may also include a second link-engaging member on the second appliance portion, wherein the linear displacement of the second flange exerts a second force on the second link-engaging member when it is linearly displaced, and wherein the second force causes the second appliance portion to be displaced relative to the first appliance portion. In this embodiment, the first flange and the second flange may be linearly displaced in substantially equal amounts in response to rotation of the drive gear. Each helical member may be coupled to the drive gear by a worm screw.

In some example embodiments, actuation and adjustment of the appliance, comprising the drive gear, helical members, actuating screw, fixed nut, may comprise a means for linearly displacing the first flange in response to a rotational input.

In a method of using the oral appliance, rotating the drive gear results in the first flange, the second flange, or both of them, being linearly displaced, and the displacement may be in substantially equal amounts due to adjustment of the single drive gear. The flanges push or exert force on link-engaging members on the lower or upper portion of the appliance, and so may advance or retract the user's mandible relative to the user's maxilla. As discussed herein, the drive gear and flange mechanism may be located on either the upper or lower portion of the oral appliance, and may be driven automatically by a motor and gear assembly mounted on the appliance, or may be driven manually, such as by a screwdriver or other device, to adjust the appliance.

There has thus been outlined, rather broadly, some of the embodiments of the apparatus for mandibular advancement of an oral appliance in order that the detailed description thereof may be better understood, and in order that the present contribution to the art may be better appreciated. There are additional embodiments of the apparatus for mandibular advancement of an oral appliance that will be described hereinafter and that will form the subject matter of the claims appended hereto. In this respect, before explaining at least one embodiment of the apparatus for mandibular advancement of an oral appliance in detail, it is to be understood that the apparatus for mandibular advancement of an oral appliance is not limited in its application to the details of construction or to the arrangements of the components set forth in the following description or illustrated in the drawings. The apparatus for mandibular advancement of an oral appliance is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein.

DETAILED DESCRIPTION

Figure 1:
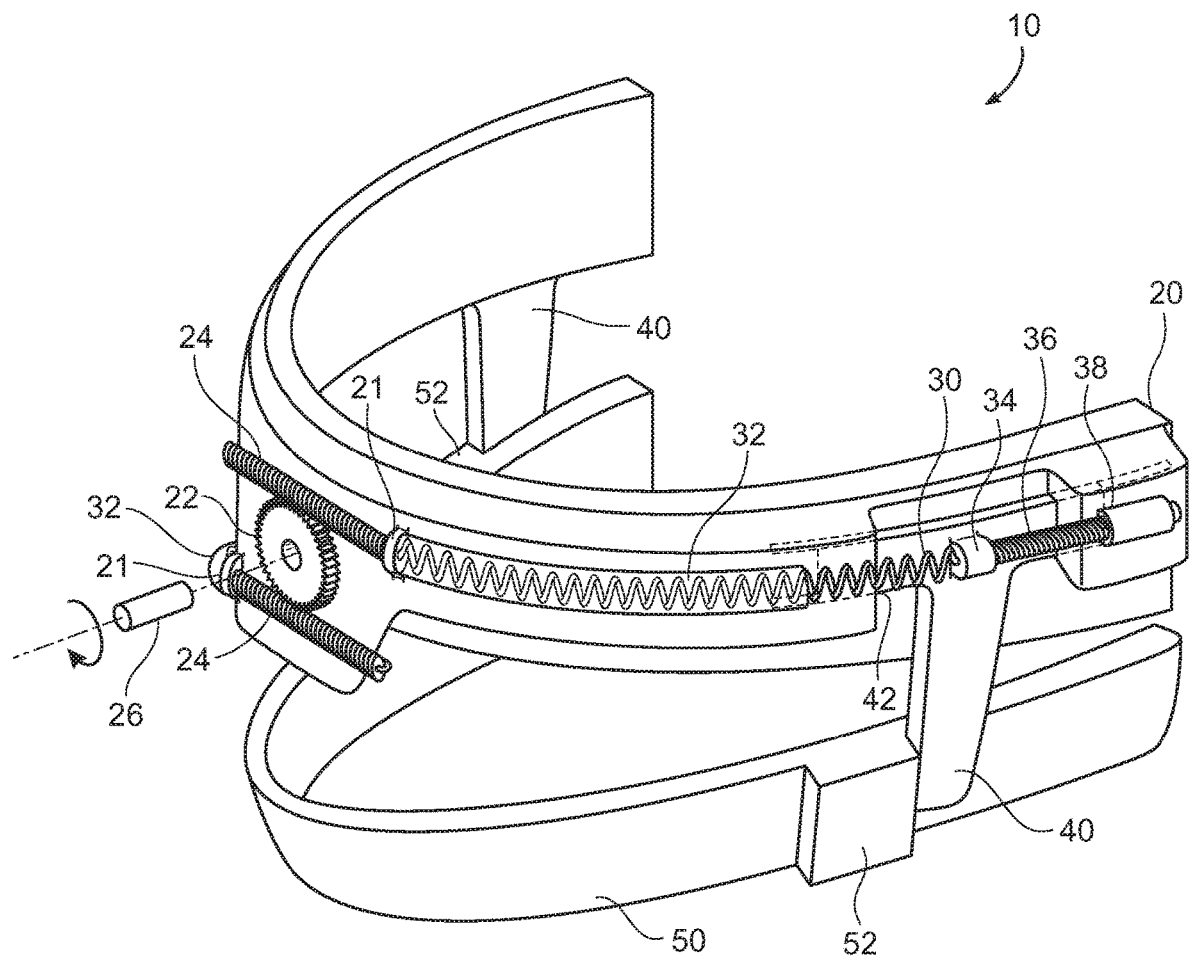
FIG. 1 is a perspective view of an apparatus for mandibular advancement of an oral appliance in accordance with an example embodiment.

A. Overview.

An example apparatus for mandibular advancement of an oral appliance 10 generally comprises a first appliance portion 20 comprising a gear assembly having a drive gear 22, wherein rotation of the drive gear 22 rotates a helical member 30 that extends from a front position to a rear position of the first appliance portion 20. A fixed nut 38 is secured proximate the rear position of the first appliance portion 20. The appliance 10 also has an actuator screw 36 with a first end threadably engaged in the fixed nut 38 and a second end rotatably coupled to the helical member 30.

A link, such as first flange 40 or other type of link 41 is slidably coupled to the first appliance portion 20, the first flange 40 or link 41 also being coupled via coupling 34 to the actuator screw 36 proximate the second end so that rotation of the actuator screw 36 causes a linear displacement of the first flange 40 as the actuator screw 36 rotates within the fixed nut 38. The fixed nut 38 is secured to the first appliance portion 20, and holds the end of actuator screw 36, wherein the opposite end of the actuator screw 36 moves when it is rotated. A second appliance portion 50 has a first link-engaging member or flange stop 52, so that the first flange 40 or link 41 exerts a force on the first link-engaging member 52 when it is linearly displaced, and wherein the force causes the second appliance portion 50 to be displaced relative to the first appliance portion 20.

In some example embodiments, the drive gear 22 comprises a worm wheel, which in turn causes worm screws 24 to rotate when the drive gear is rotated by a drive element or shaft 26, such as a screwdriver or the shaft of a drive motor. Further, the first appliance portion may comprise a maxillary portion 20 and the second appliance portion may comprise a mandibular portion 50. Alternatively, the first appliance portion may comprise a mandibular portion 50 and the second appliance portion may comprise a maxillary portion 20.

In an example embodiment, the appliance can include a second helical member 30 that extends from a front position to a rear position of the first appliance portion 20, a second fixed nut 38 secured proximate the rear position of the first appliance portion 20, and a second actuator screw 36 having a first end threadably engaged in the second fixed nut 38 and a second end rotatably coupled to the second helical member 30. In the embodiment, a second flange 40 or link 41 is slidably coupled to the first appliance portion 20, the second flange 40 or link 41 also being coupled via coupling 34 to the second actuator screw 36 proximate the second end so that rotation of the second actuator screw 36 causes a linear displacement of the second flange 40 or link 41 as the second actuator screw 36 rotates within the second fixed nut 38.

The embodiment may also include a second link-engaging member 52 on the second appliance portion 50, wherein the linear displacement of the second flange 40 or link 41 exerts a second force on the second link-engaging member 52 when it is linearly displaced, and wherein the second force causes the second appliance portion 50 (e.g., the mandibular portion) to be displaced relative to the first appliance portion 20, which may be the maxillary portion of the appliance. In this embodiment, the first flange 40 or link 41 and the second flange 40 or link 41 may be linearly displaced in substantially equal amounts in response to rotation of the drive gear 22. Each helical member 30 may be coupled to the drive gear by a worm screw 24. The helical members 30 are relatively flexible, so that they may conform substantially to a user's jaw within channels 32 in the upper or lower portion of the appliance 10.

The helical members 30 also flex along their length as the actuator screws 36 move forward and back to advance or retract the mandibular portion 50 of the appliance 10. When the drive gear 22 is rotated, each worm screw 24 rotates by about the same amount, in opposite directions. To account for this, the actuator screws 36 on either side of the appliance 10 may have reverse threads from each other, so that clockwise rotation on one side, and counter-clockwise rotation on the other side of the appliance 10 results in forward (or reverse) linear displacement of each flange 40 or link 41, one on each side of the appliance. The helical members 30 transfer the rotation of the worm screws 24 at the front of the appliance 10 to the actuator screws 36 at the rear portion of the appliance 10, the helical members 30 being rotationally coupled to both the worm screws 24 and the actuator screws 36.

In some example embodiments, actuation and adjustment of the appliance, comprising the drive gear 22, helical members 30, actuating screws 36, fixed nuts 38, may comprise a means for linearly displacing the first flange 40 or link 41 and the second flange 40 or link 41 in response to a rotational input.

In a method of using the oral appliance, rotating the drive gear 22 results in the first flange 40 or link 41, the second flange 40 or link 41, or both of them, being linearly displaced, and the displacement may be in substantially equal amounts due to adjustment of the single drive gear. As an example, rotation of the drive gear 22 provides for a single input point or action that results in a flange or link exerting force on the link-engaging member on the mandibular portion 50, resulting in the mandibular portion 50 being advanced forward relative to the upper, maxillary portion 20 of the appliance. This direction can of course also be reversed by driving gear 22 in the opposite direction.

B. Oral Appliance.

As shown generally in the figures, and particularly in FIGS. 1 and 15-19, the oral appliance 10 (which may be commonly known as a mouth guard) is generally comprised of 2 sections—a biocompatible covering for the teeth in the maxilla (upper jaw) and the other for the teeth in the mandible (lower jaw). For ease of reference, the upper, maxillary mouth guard or maxillary portion of the appliance 10 may be referred to as the first portion 20 or the maxillary portion 20, although in an alternative embodiment, either the upper or lower portion of the appliance may include the actuation components. In other words, the upper and lower portions of the appliance may be substantially interchangeable, so long as the appliance 10 is able to advance or retract the mandibular portion 50 relative to the maxillary portion 20.

The biocompatible covering of each portion may preferably be custom-molded to fit over an individual's teeth, although various other non-custom designs may be utilized for the oral appliance 10. The maxillary and mandibular mouthguard portions could cover a portion or all of an individual's teeth. The function of the oral appliance 10 is to provide protection and enough surface area so as to allow an affixed mechanical unit comprising gears and other components to safely pull forward (advance) or retract the mandibular portion 50 relative to the maxillary portion 20 of the device. The gear assembly may be affixed onto or integrally formed or attached to the maxillary mouth guard portion, however, in other embodiments, the assembly may be part of, on, or attached to the mandibular portion 50.

The appliance 10 may be custom manufactured by relying on a physical model or digital impression of the individual's teeth. In other cases, the appliances 10 may come in standard configurations, but are then heated (via boiling) to conform to an individual's teeth. Upon cooling, the appliance 10 retains its molded shape and closely matches the individual's teeth.

In an example embodiment, the frontal surface of the maxillary portion 20 is adhesively or mechanically attached to a unit comprising the gear assembly, comprising drive gear 22 (such as a worm wheel) and worm screws 24, one above and one below the drive gear 22. A helix member 30 is positioned within a telescoping unit housing or channel 32. The maxillary portion 20 and the mandibular portion 50 may be separate sections or units, but non-adhesively couple to one another via flanges 40, or, in an alternative embodiment, links 41.

Figure 4:
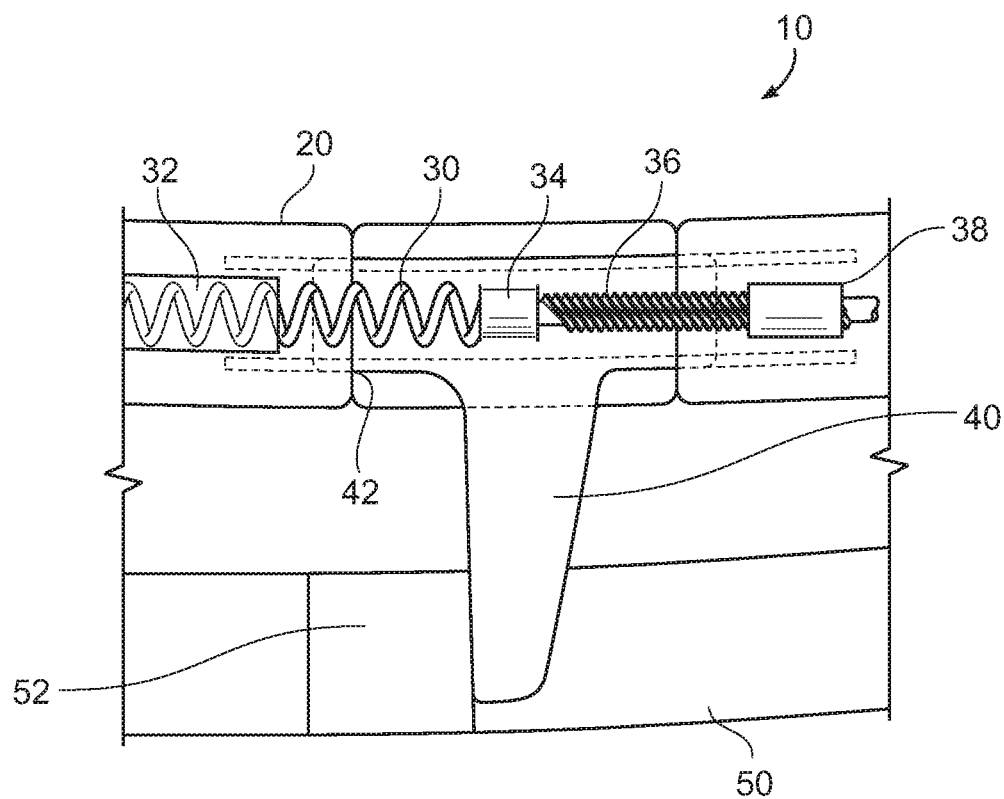
FIG. 4 is another detail view of a portion of an apparatus for mandibular advancement of an oral appliance in accordance with an example embodiment.
Figure 5:
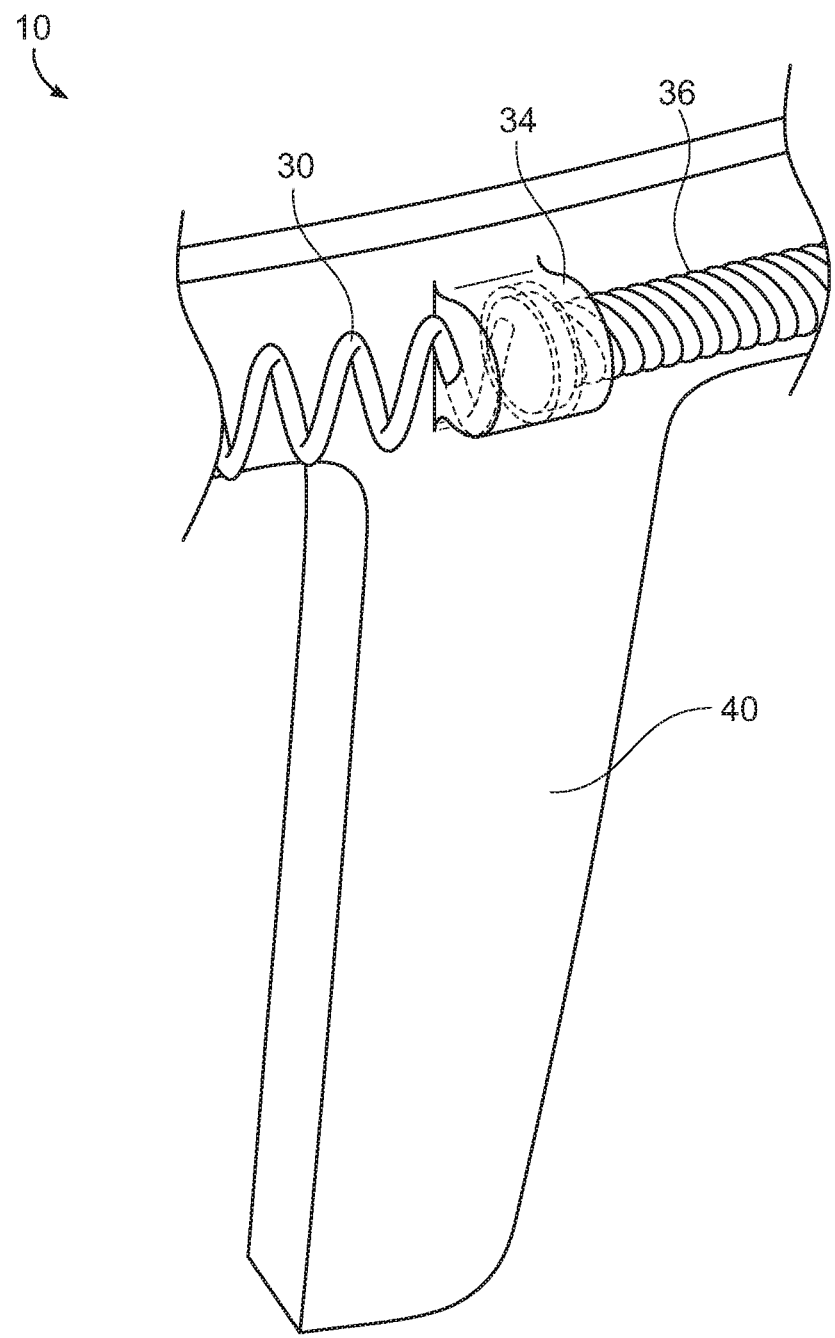
FIG. 5 is another detail view of a portion of an apparatus for mandibular advancement of an oral appliance in accordance with an example embodiment.
Figure 6:
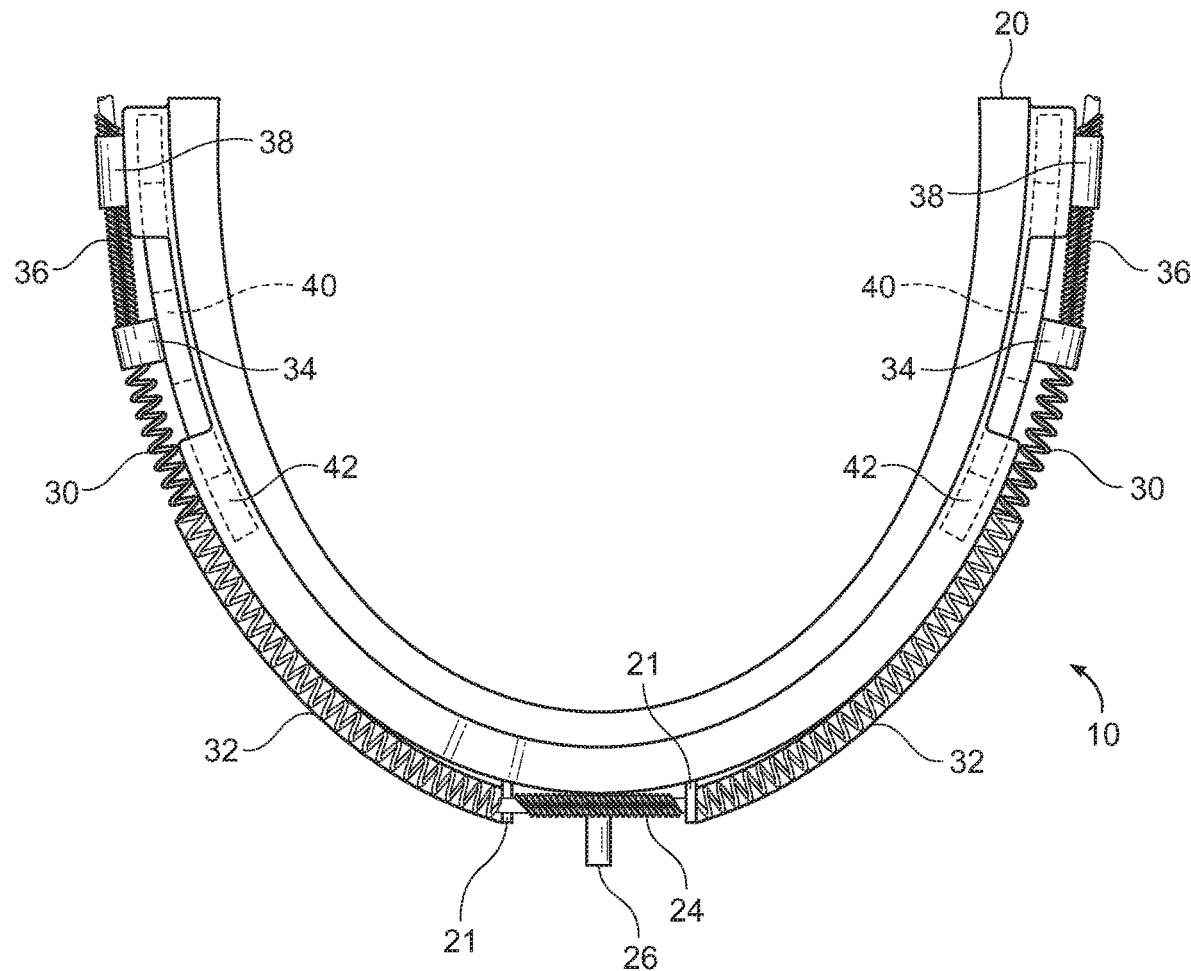
FIG. 6 is a top view of an apparatus for mandibular advancement of an oral appliance in accordance with an example embodiment.
Figure 7:
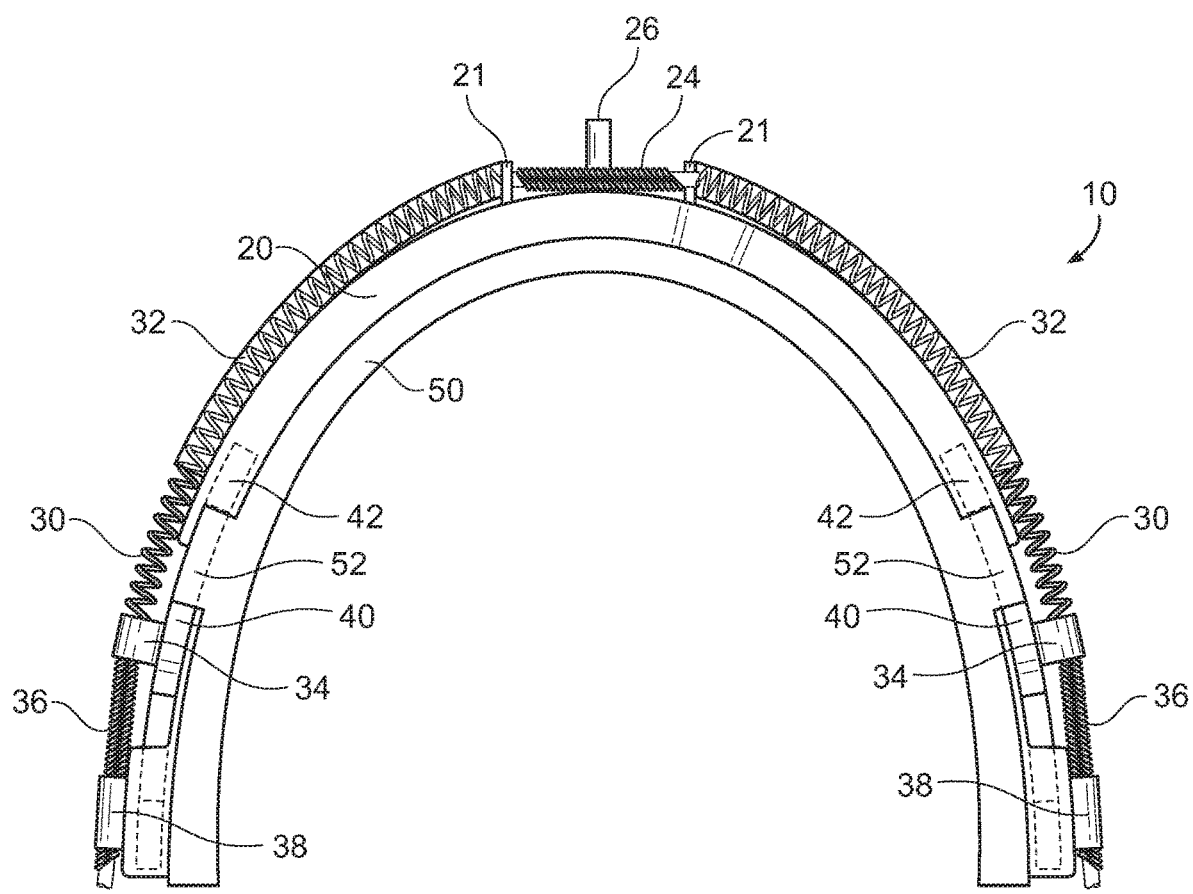
FIG. 7 is a bottom view of an apparatus for mandibular advancement of an oral appliance in accordance with an example embodiment.

On the first appliance portion 20, rotation of the drive gear 22 rotates one or two helical members 30 that extend from a front position to a rear position of the first appliance portion 20. The helical member 30 is held within a channel 32, which allows the helical member 30 (one on each side of the appliance, typically) to rotate freely, generally without coming in contact with the user's mouth. A fixed nut 38 is secured at or near the rear position of the first appliance portion 20. The fixed nut 38 does not move relative to the portion 20, although actuation screw 36 advances and retracts within the nut as the actuation screw is rotated. The actuator screw 36 has a first end threadably engaged in the fixed nut 38 as shown in FIGS. 1 and 4, and a second end rotatably coupled to the helical member 30.

A pair of flanges 40 are slidably coupled to the first appliance portion 20, as shown for example in FIGS. 1, 4-5, 8-13, 15, and 17, each flange 40 also being coupled via flange couplings 34 to the actuator screws 36 near the second end so that rotation of the actuator screw 36 causes a linear displacement of the flanges 40 as the actuator screws 36 rotate within the fixed nuts 38. Each flange 40 or link 41 may be positioned within a flange slot 42 that generally holds each flange or link in place while allowing them to slide back and forth relative to the first portion 20 of the appliance 10. Each fixed nut 38 is secured toward the back of each side of the first appliance portion 20, and engages the end of actuator screws 36, and the opposite ends of the actuator screws 36 move linearly when they are rotated.

A second appliance portion 50 (e.g., the mandibular portion 50 of the appliance 10) has a first link-engaging member or flange stop 52, so that the flanges 40 exert a force on the first link-engaging member 52 when it is linearly displaced, and the force causes the second appliance portion 50 to be displaced relative to the first appliance portion 20.

Figure 14:
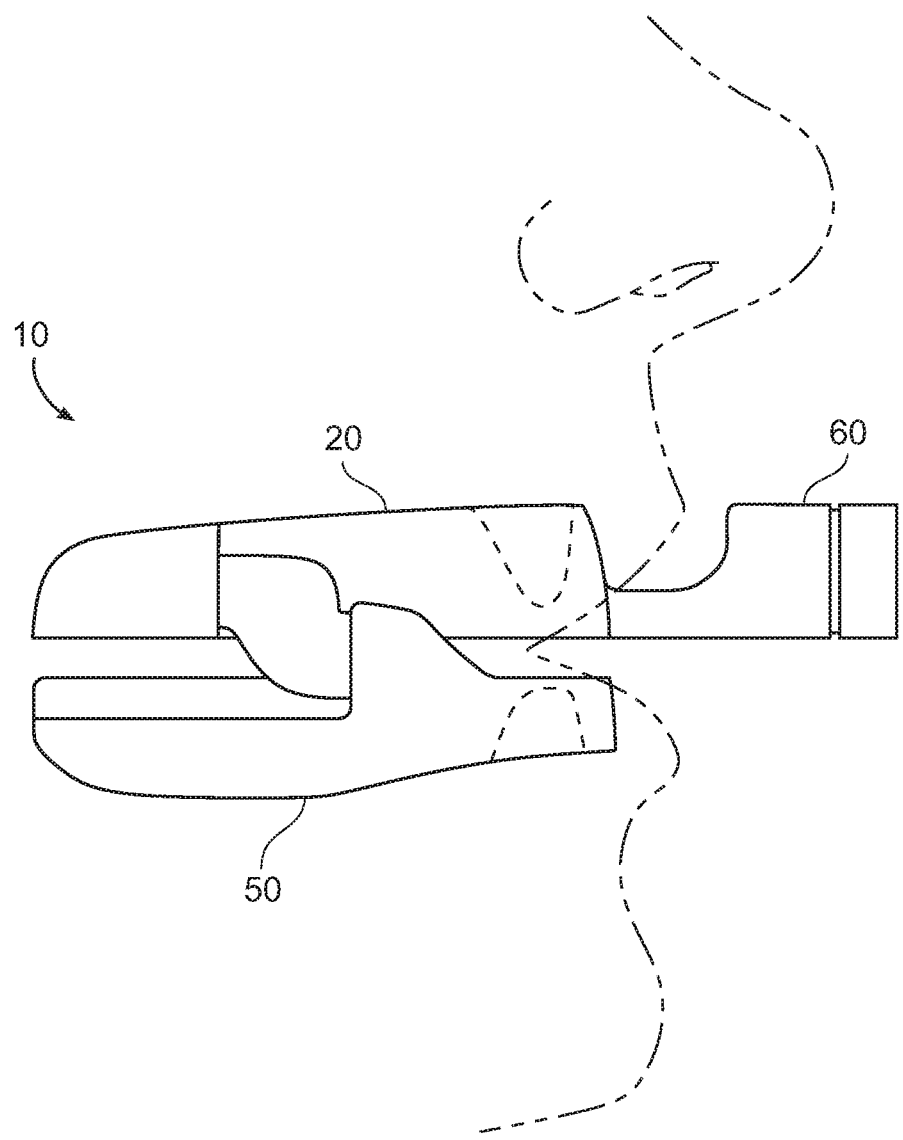
FIG. 14 is a side view of an apparatus for mandibular advancement of an oral appliance in accordance with another example embodiment.

In some example embodiments, the drive gear 22 comprises a worm wheel, which in turn causes worm screws 24 to rotate when the drive gear is rotated by a drive element or shaft 26, such as a screwdriver or the shaft of a drive motor. As shown in FIG. 14, a battery-powered or motor-powered drive unit 60 may be attached or molding in the upper or lower portion of the appliance, so that the drive unit may manually or automatically be caused to rotate the drive gear 22. The drive unit 60 may include a battery, motor, and a shaft 26. It may also include electronic circuitry for receiving inputs and producing commands to cause adjustment of the appliance as described here. Further, the first appliance portion may comprise a maxillary portion 20 and the second appliance portion may comprise a mandibular portion 50. Alternatively, the first appliance portion may comprise a mandibular portion 50 and the second appliance portion may comprise a maxillary portion 20.

Figure 16:
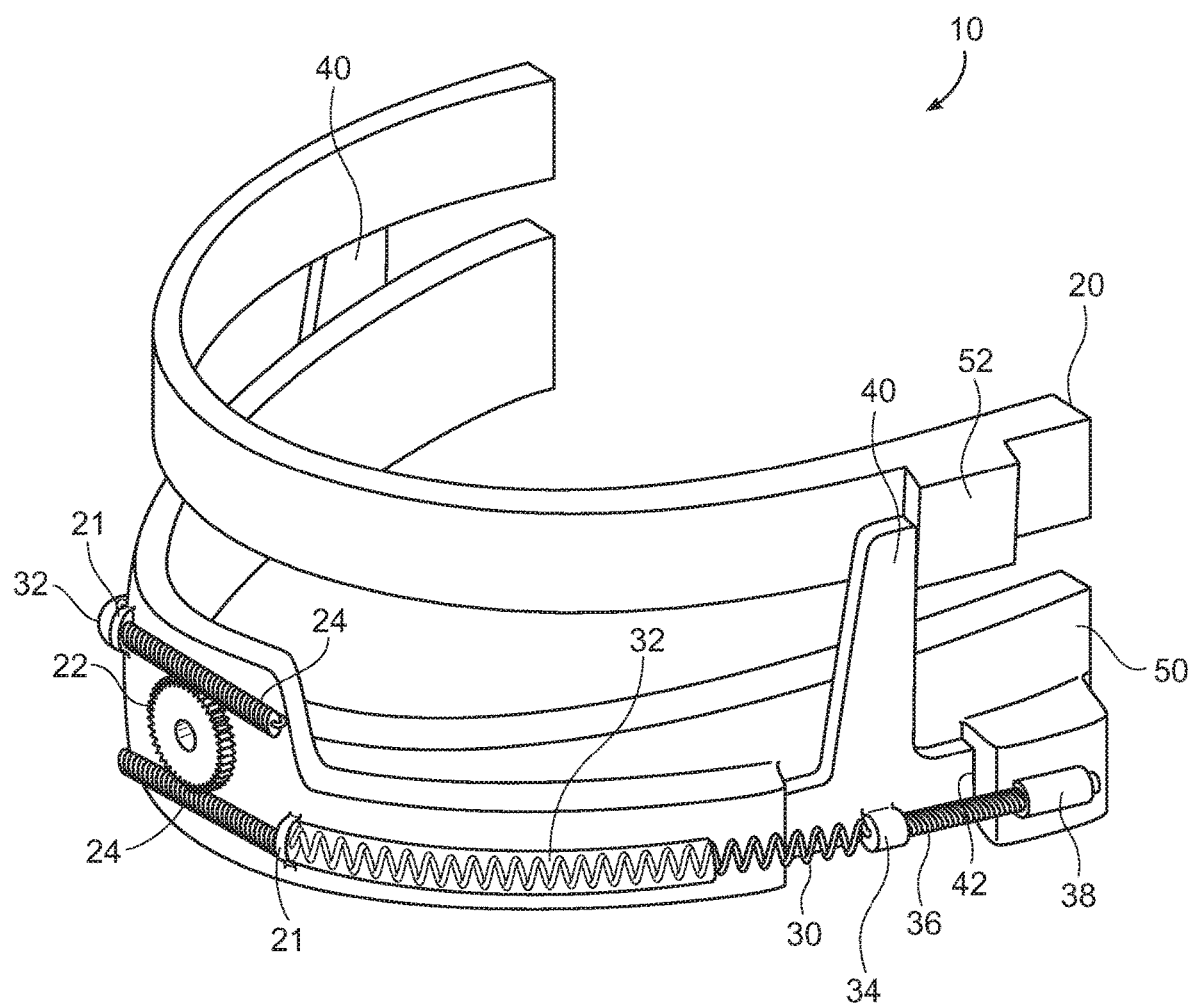
FIG. 16 is another front perspective view of an apparatus for mandibular advancement of an oral appliance in accordance with another example embodiment.
Figure 17:
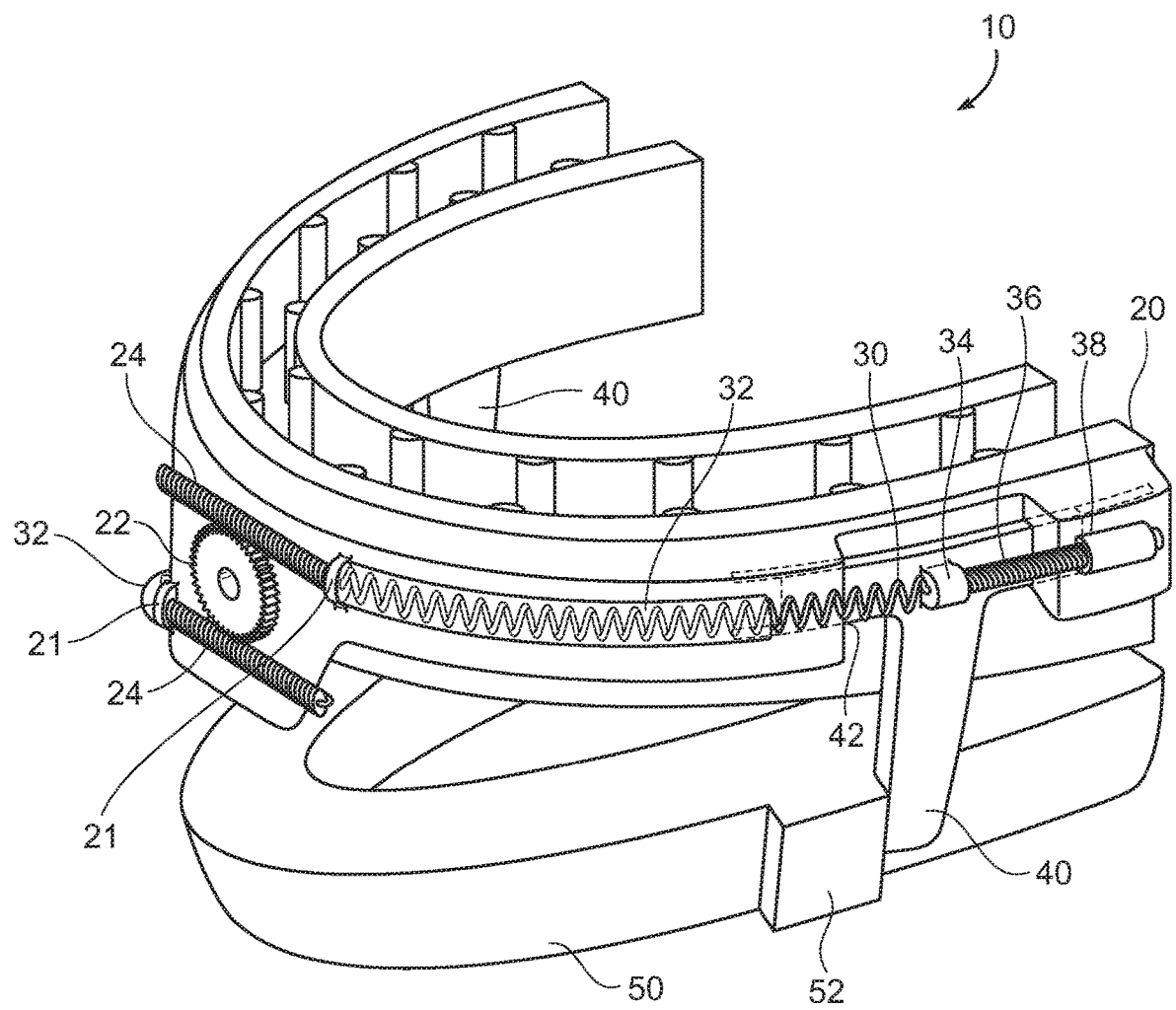
FIG. 17 is a front perspective view of an apparatus for mandibular advancement of an oral appliance in accordance with another example embodiment.

In other possible example embodiments, as shown in FIG. 16, the telescoping unit channel or housing 32, the gear assembly, and other drive components as described above is adhesively or mechanically attached, or integrally formed with, the mandibular portion 50. The maxillary portion 20 in such an embodiment is coupled to the mandibular portion 50 via flanges 40, or links 41. In this embodiment, in order to advance the mandibular portion 50, the flanges 40 or other links 41 are driven rearward, which pushes or forces link-engaging members 52 in maxillary portion 20 rearward relative to portion 50. Accordingly, since portion 20 is stationary, mandibular portion 50 will move forward.

C. Gear Assembly.

The gear assembly is affixed on, or may be part of, the maxillary portion 20, and consists of gears and screws that engage with an external motor shaft or manual tool, such as a screwdriver 26. The gear assembly may comprise a drive gear 22, such as a single worm wheel 22 that engages a pair of worm screws 24, one for each side of the user's jaw (right and left); however, multiple interlocking gears could also be used based on desired displacement, torque and rotational speed. Some of the figures (e.g., FIGS. 1-3, etc.) show the gears exposed for clarity and explanation purposes, but in practice the gears, such as worm drive gear 22 and worm screws 24, as well as the alternate gear configurations described here, may be within a housing or enclosure, and may also include other components to hold the gear assembly in place, as shown for example in FIG. 14. The worm screws 26 are coupled individually to flexible helixes 30. The function of the gear assembly is to translate the rotational motion of a drive motor shaft 26 or screwdriver 26 into appropriate rotation and linear displacement of the connected flexible helix 30 on each side of the appliance 10.

Figure 2:
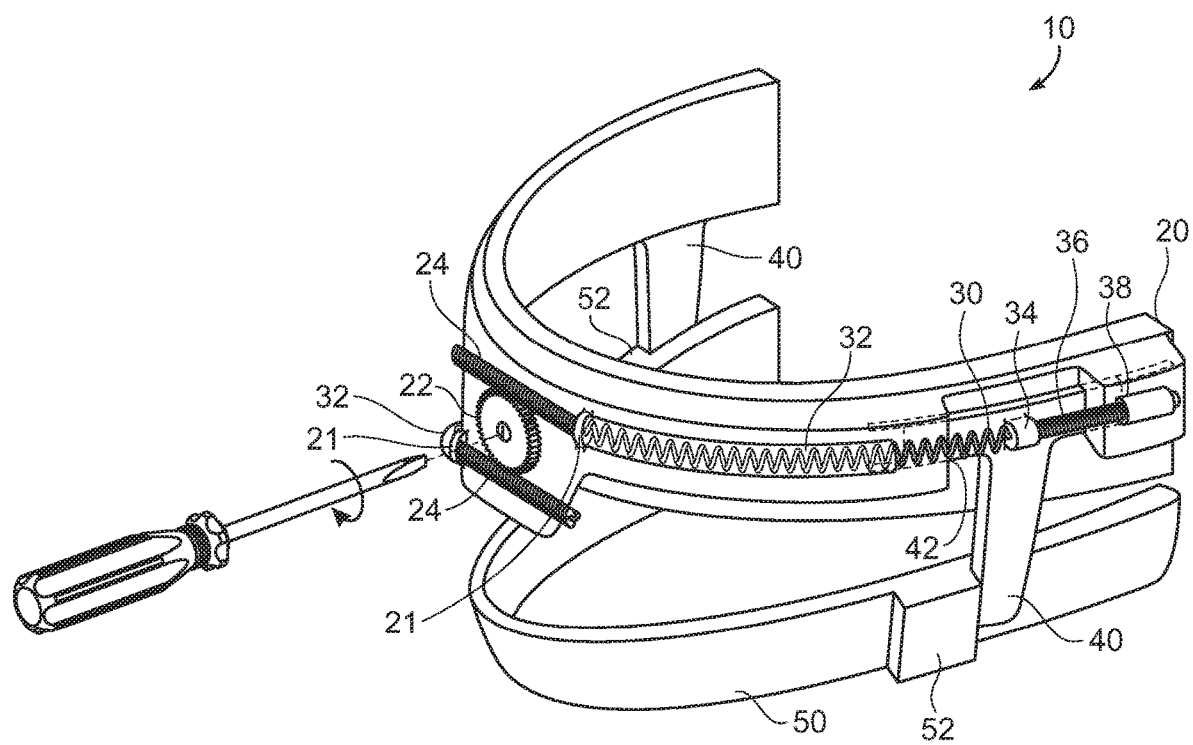
FIG. 2 is another perspective view of an apparatus for mandibular advancement of an oral appliance in accordance with an example embodiment
Figure 3:
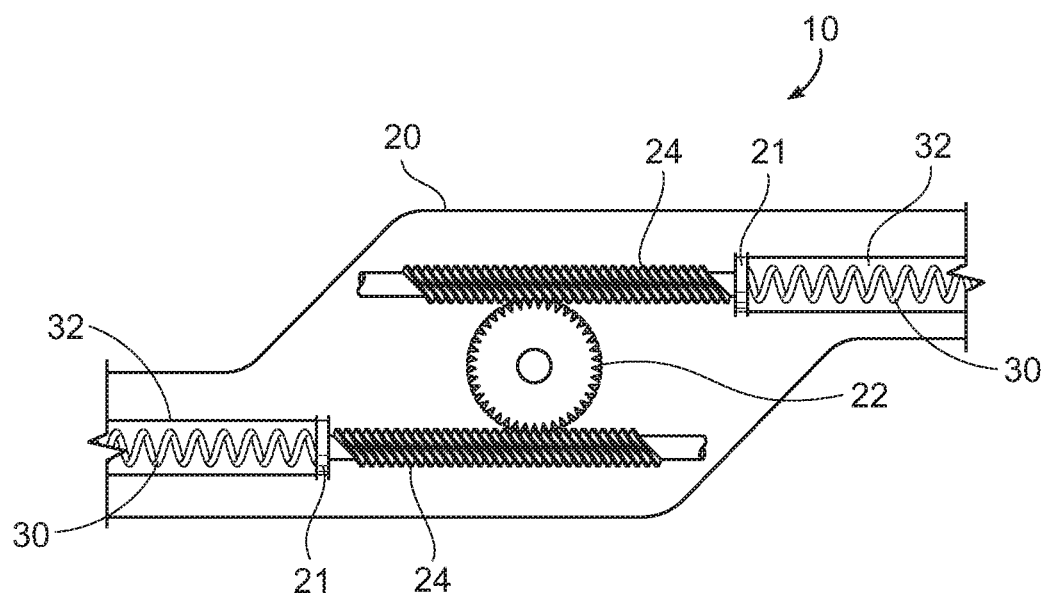
FIG. 3 is a detail view of a portion of an apparatus for mandibular advancement of an oral appliance in accordance with an example embodiment.

In an example embodiment, the gear assembly comprises one worm wheel or gear 22 coupled to a pair of worm screws 24, one for the left side and the other for the right side of the appliance 10, corresponding to each side of the user's jaw. As shown in FIGS. 1-3, for example, there is one worm screw 24 above the worm wheel 22, and driven by the wheel. As also shown, the worm screw 24 above the gear 22 drives the helical member 30 along the left side of the maxillary portion 20 through rotation. Similarly, there is another worm screw 24 below the worm wheel 22 that will be driven in the opposite rotational direction when the worm wheel 22 is rotated. This worm screw 24 is coupled to the left side of the appliance through helical member 30 on the left side of maxillary portion 20. The rotation of both worm screws is coupled to the actuator screws 36 at the rear of the device.

Alternatively to a single drive gear 22, multiple interlocking gears could also be used based on the desired displacement, torque and rotational speed that will be coupled to the actuator screws 36. The left worm screw 24 and the right worm screw 24 are on opposite ends of the worm gear 22 (e.g., one above and one below it), such that when the worm gear 22 rotates, it couples with both the worm screws 24, and they each rotate in opposite directions, as best shown in FIG. 3.

In an example embodiment, the worm gear 22 is designed to engage with and be driven by an external motor shaft or screw-driver 26, as shown for example in FIGS. 1, 2, and 14. The worm screws 24 are coupled individually to flexible helical members 30, also one per side of the appliance 10. The left-side worm screw 24 connects to the left-side helical member 30 via a left-side screw coupling 21; similarly, the right-side worm screw 24 connects to the right-side helix via the right-side screw coupling 21. The function of the gear assembly is to translate the rotational motion of a screw-driver 26 or motor shaft 26 into appropriate rotational motion of each connected flexible helical member.

Worm gear 22 may be comprised of one gear or multiple interlocking gears. Worm screws 24 may be placed on opposite ends or sides of the single worm gear 22, but in example embodiments with multiple worm gears, the screws 24 would be coupled in such fashion so as to permit those screws to simultaneously rotate in opposite directions to each other when the worm gear 22 is rotated. In other example embodiments, additional components could be utilized to house the gear assembly in the telescoping unit channel 32. There could also be additional components used to connect the worm gear 22 to a manual screwdriver or motor-shaft 26.

D. Helix Assembly/Helical Members

The helix assembly comprises mechanical spring-like flexible helical members 30 (one on the left and one on the right of the appliance 10) which can bend and flex around the curvature of the jaw, which is matched by the curvature of the maxillary portion 20 or mandibular portion 50 of the appliance. The assembly is completed by a matching pair of channels 32 in which the helical members are contained, but may rotate freely. In addition to rotation, the helical members 30 may move linearly within the channels 32, which movement or displacement will occur as the system is actuated, as discussed further below.

The function of each helix assembly is to translate the rotation of the worm screw 24 connected at its front end to rotational motion required to drive the telescoping screws 36 connected at their other end, toward the rear or back position of the appliance 10. There are 2 helix assemblies in the design, one to operate the telescoping actuator screw 36 on the left side and the other for the screw 36 on the right side of the jaw. Each helical member is encased or enclosed in a tube-like protective housing or channel 32 which also provides it structural strength while it flexes and rotates when the screws rotate.

E. Telescoping Assembly.

The telescoping assembly comprises a movable flange 40 or hook which is coupled via coupling 34 to a telescoping or actuator screw 36 and fixed nut 38. Each actuator screw 36 is connected to a flexible helical member 30, and rotates as the helix rotates. The rotational motion of the helical members 30 and the telescoping screws 36 is converted into linear displacement of the flange 40 or hook. The flange 40 or hook are engaged with a rigid stopper or link-engaging member 52 affixed to the mandibular portion 50 of the appliance 10. The function of the flange engaging member 52 is to be linearly displaced forward (advance) or retract the mandible, depending on the linear displacement of the flange 40 or hook. FIG. 4 shows greater detail of the engagement of the flange 40 and link-engaging member 52.

The telescoping assembly comprises an actuator screw 36 connected to the left or right-side helical member 30. The helix-to-telescoping screw coupling also connects to the flange 40 via a coupling 34 as shown in greater detail in FIG. 5. Each telescoping actuator screw 36 threads into a fixed nut 38. The flange 40 (or a band-shaped portion of an alternative link 41) slides over or within a flange slot 42. A link-engaging member 52 is affixed to the mandibular portion 50.

Figure 18:
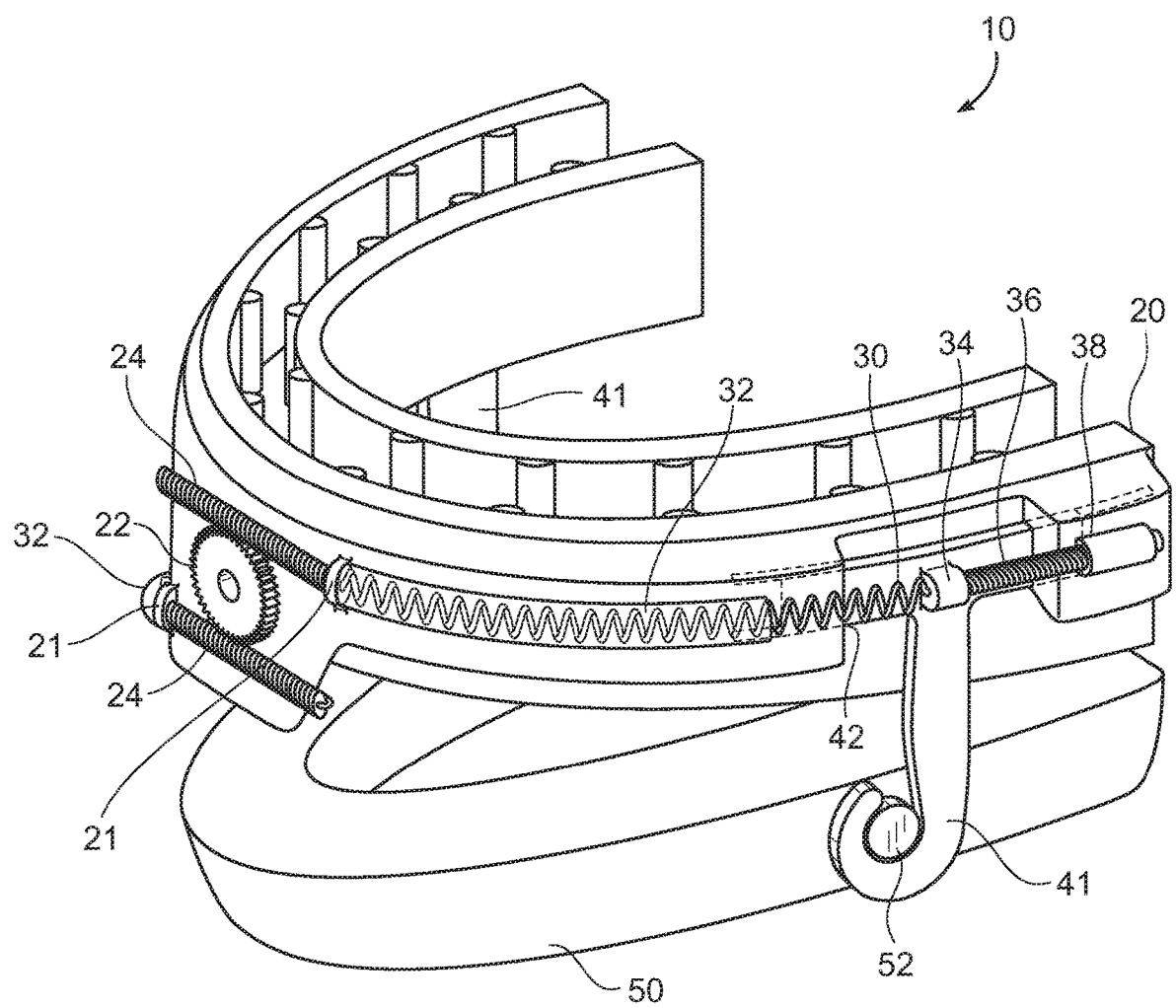
FIG. 18 is a front perspective view of an apparatus for mandibular advancement of an oral appliance in accordance with another example embodiment.
Figure 19:
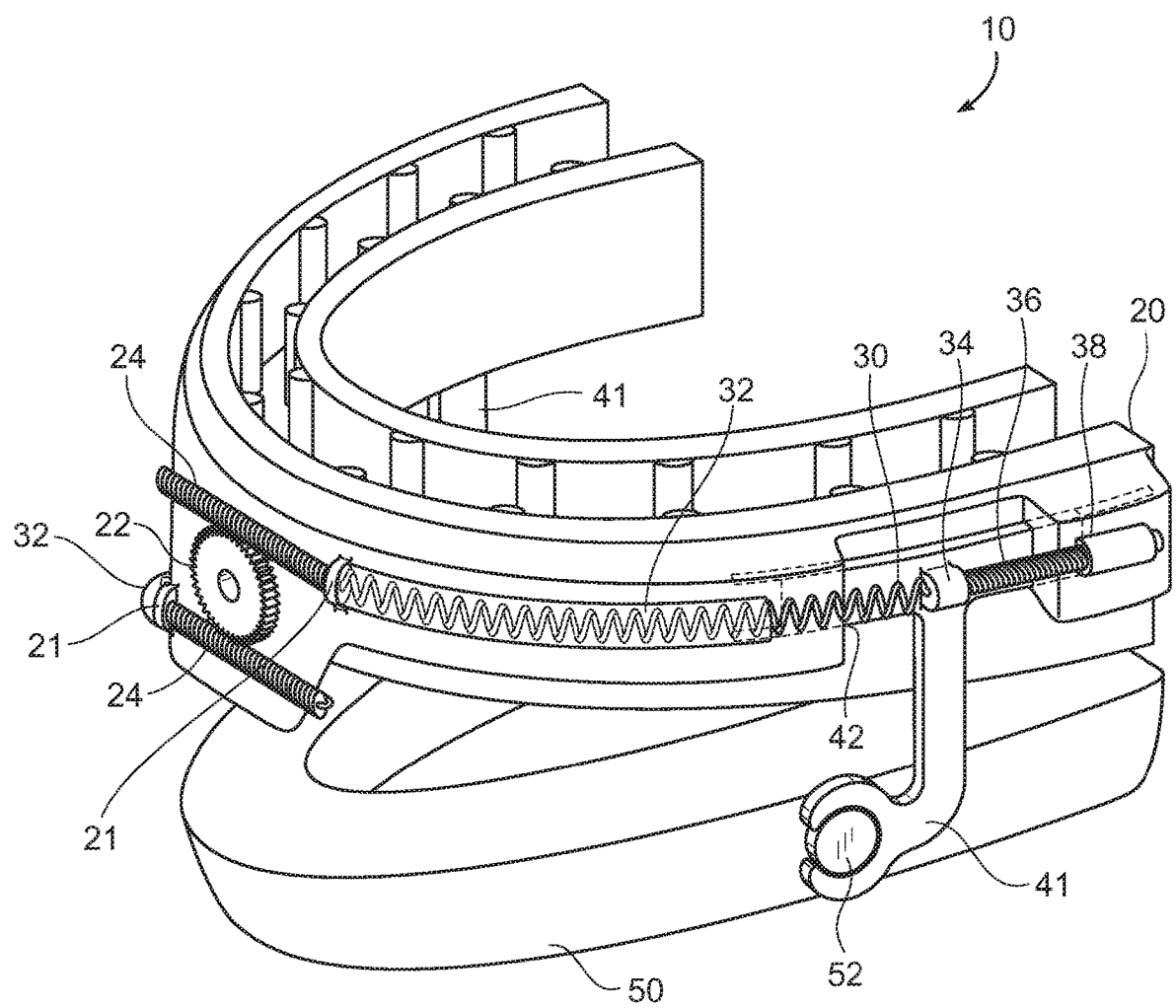
FIG. 19 is a front perspective view of an apparatus for mandibular advancement of an oral appliance in accordance with another example embodiment.

In other embodiments, as shown in FIGS. 18 and 19, a link 41, such as a hook (FIG. 18) or snap link (FIG. 19) can be utilized instead of a flange 40, and such a link 41 can engage link-engaging member 52 to couple the maxillary portion 20 to the mandibular portion 50. Since the hook or snap link is able to exert force and displace the mandibular portion or maxillary portion as described herein, the appliance will operate similarly to embodiments that use a flange 40 to push the link-engaging member 52.

F. Operation of Preferred Embodiment.

In use, rotation of a worm gear or drive gear 22 rotates two helical members 30 that extend from the front position to a rear position of the first appliance portion 20. Each helical member 30 is rotationally coupled to a worm screw 24, and also to an actuator screw 36 at the rear position of the appliance. A fixed nut 38 is secured at or proximate to the rear position of the first appliance portion 20. Each actuator screw 36 has a first end threadably engaged in a fixed nut 38 and a second end rotatably coupled to the helical member 30. Once a worm screw is rotated by the drive gear 22, its corresponding helical member 30 and actuator screw 36 also rotate, in the same direction, due to the rotational couplings between each component.

A pair of flanges 40 are slidably coupled to the first appliance portion 20, each flange 40 also being coupled by coupling 34 to the actuator screw 36 proximate the second end so that rotation of the actuator screw 36 causes a linear displacement of the flange 40 as the actuator screw 36 rotates within the fixed nut 38. The fixed nut 38 is secured to the first appliance portion 20, and holds the end of actuator screw 36 in a fixed position, which causes the opposite end of the actuator screw 36, and also the corresponding flange 40, to move linearly when the actuator screw is rotated. Each helical member 30 may freely rotate within, and move linearly within, a tube-like channel 32 formed in the maxillary portion 20, as shown in FIGS. 1-13, 15, and 17-19, or in the mandibular portion 50, as shown in FIG. 16.

A second appliance portion 50 (e.g., a mandibular portion) has a first link-engaging member or flange stop 52, so that the flanges 40 exert a force on the first link-engaging member 52 when it is linearly displaced, and wherein the force causes the second appliance portion 50 to be displaced relative to the first appliance portion 20.

In some example embodiments, the drive gear 22 comprises a worm wheel, which, when rotated, causes worm screws 24 to rotate, for example, when the drive gear is rotated by a drive element or shaft 26, such as a screwdriver or the shaft of a drive motor. Further, the first appliance portion may comprise a maxillary portion 20 and the second appliance portion may comprise a mandibular portion 50. Alternatively, the first appliance portion may comprise a mandibular portion 50 and the second appliance portion may comprise a maxillary portion 20.

In an example embodiment, the appliance can include a second helical member 30 that extends from a front position to a rear position of the first appliance portion 20, a second fixed nut 38 secured proximate the rear position of the first appliance portion 20, and a second actuator screw 36 having a first end threadably engaged in the second fixed nut 38 and a second end rotatably coupled to the second helical member 30. In the embodiment, a second flange 40 is slidably coupled to the first appliance portion 20. The second flange 40 may also be coupled to the second actuator screw 36 proximate the second end so that rotation of the second actuator screw 36 causes a linear displacement of the second flange 40 as the second actuator screw 36 rotates within the second fixed nut 38.

As shown in the figures, the adjustment system may be substantially symmetrical, although the actuator screws 36 will be different, for the following reasons. Symmetrical in this instance refers to substantially similar elements and actions being found and operated on the left side and on the right side of the appliance 10.

As mentioned above, when the worm wheel or drive gear 22 is rotated, it creates a single adjustment point that results in substantially equal displacement of the mandibular portion 50 of the appliance 10 relative to the upper or maxillary portion 20. This configuration eliminates the need to have two separate screw or drive assemblies in order to adjust the appliance 10. As for actuation, suppose gear 22 is rotated clockwise. As mentioned above, the gear may be manually driven or may be motor driven. Worm screw 24 at the top of gear 22 may rotate clockwise as well, although worm screw 24 at the bottom, which adjusts the right side of the appliance, will then rotate counter-clockwise.

Accordingly, for this input, the actuator screw 36 on the left side of the device may be a right-handed screw. Since it is threaded into fixed nut 38, the screw 36, and more particularly the coupling 34 which moves with screw 36, will move rearward. This actuation should be duplicated at the opposite side of the appliance, so the actuator screw 36 on the right side must be left-handed, since it will rotate in the opposite direction of its counterpart.

If the appliance is actuated in the direction noted above, the coupling 34, and thus the flanges 40, will be linearly displaced rearward, due to the actuator screws 36 moving farther into fixed nuts 38. This will allow or cause the mandibular portion 50 to also move rearward, due to the resting position of the user's mandible. In other words, the link-engaging members 52 on either side of appliance 10 will "follow" the flanges 40 rearward due to the actuation input on gear 22.

Figure 8:
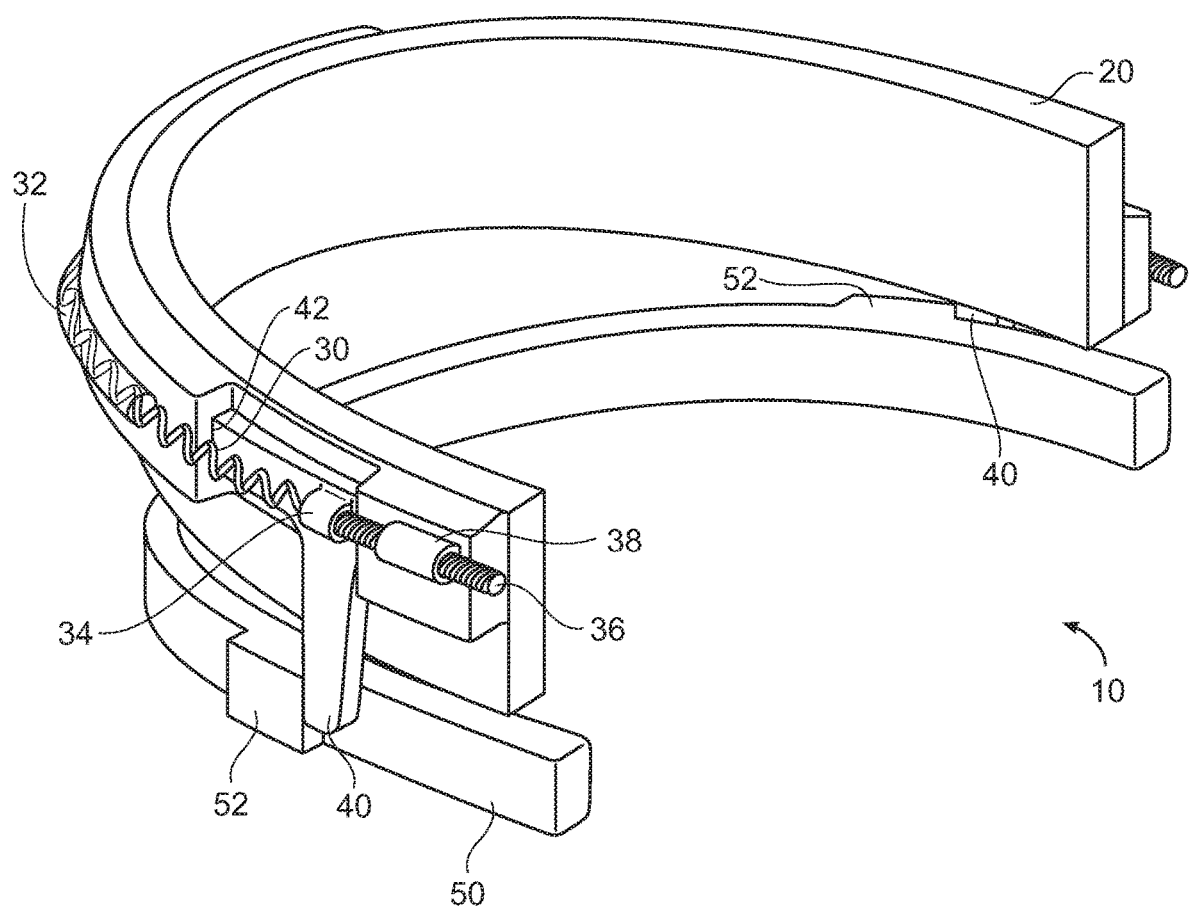
FIG. 8 is a rear perspective view of an apparatus for mandibular advancement of an oral appliance in accordance with an example embodiment.
Figure 9:
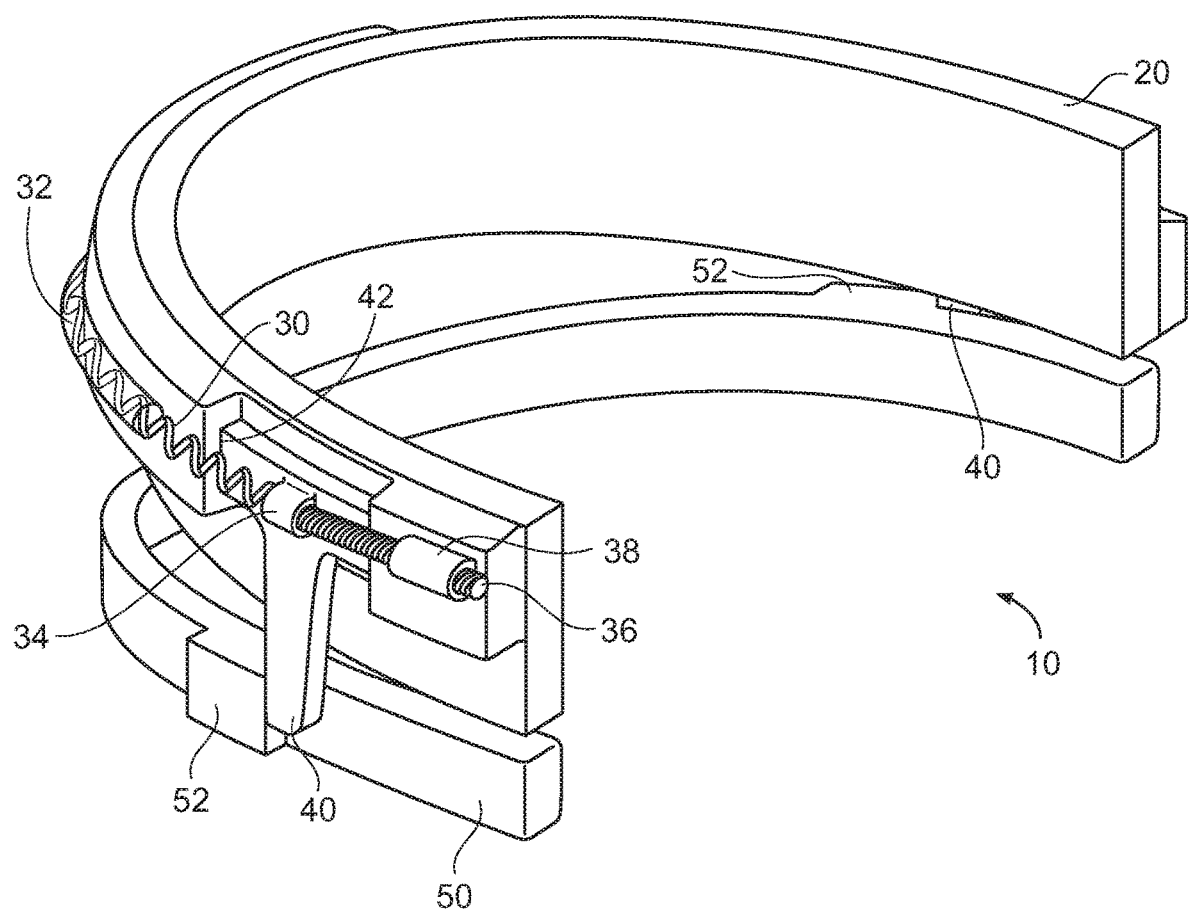
FIG. 9 is another rear perspective view of an apparatus for mandibular advancement of an oral appliance in accordance with an example embodiment.
Figure 10:
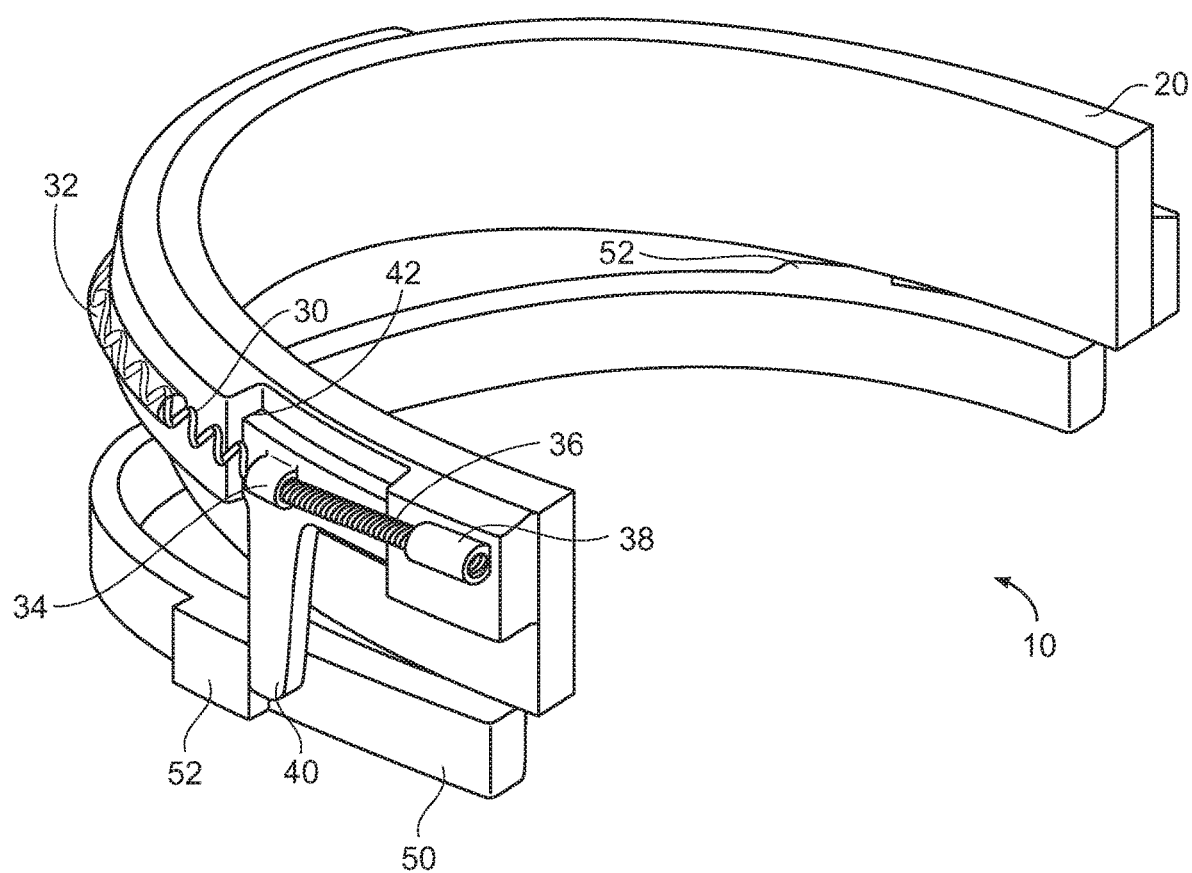
FIG. 10 is another rear perspective view of an apparatus for mandibular advancement of an oral appliance in accordance with an example embodiment.
Figure 11:
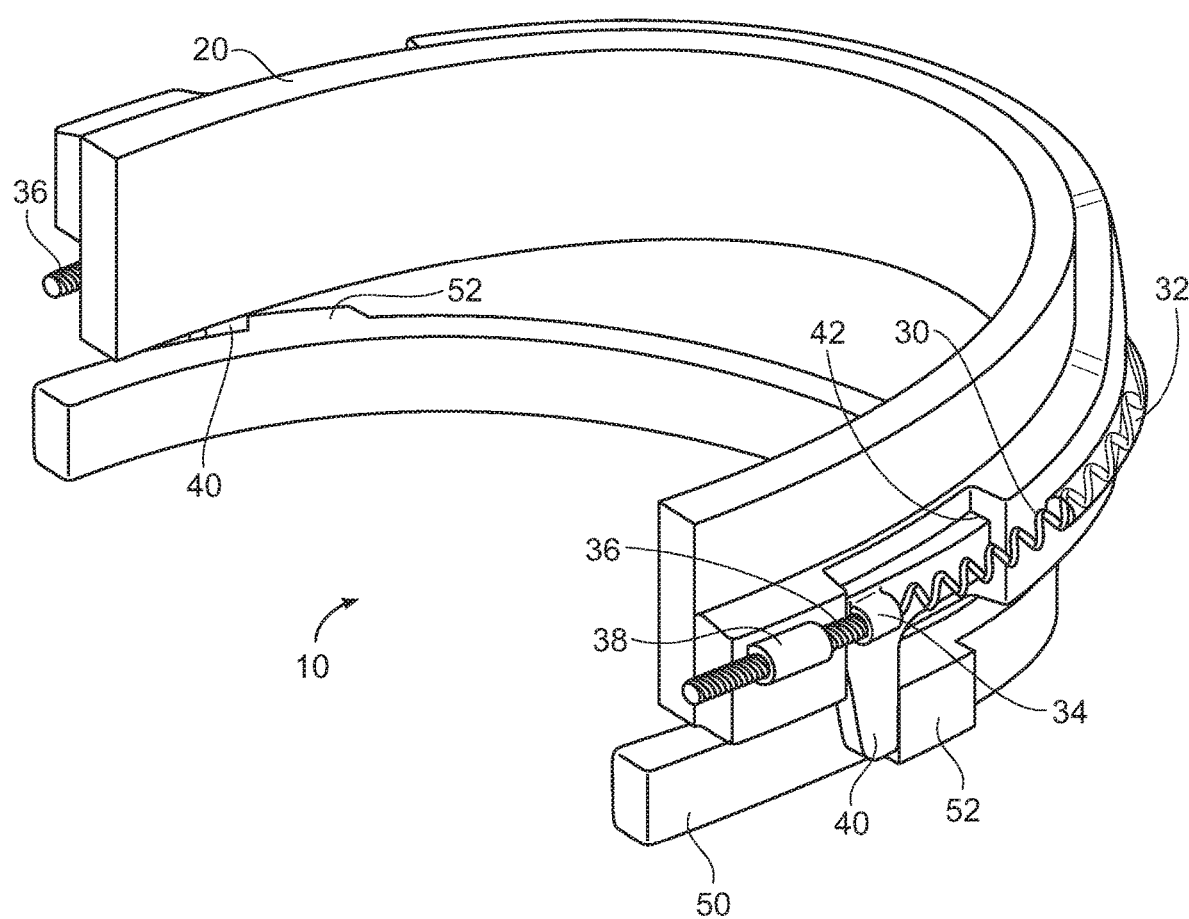
FIG. 11 is another rear perspective view of an apparatus for mandibular advancement of an oral appliance in accordance with an example embodiment.
Figure 12:
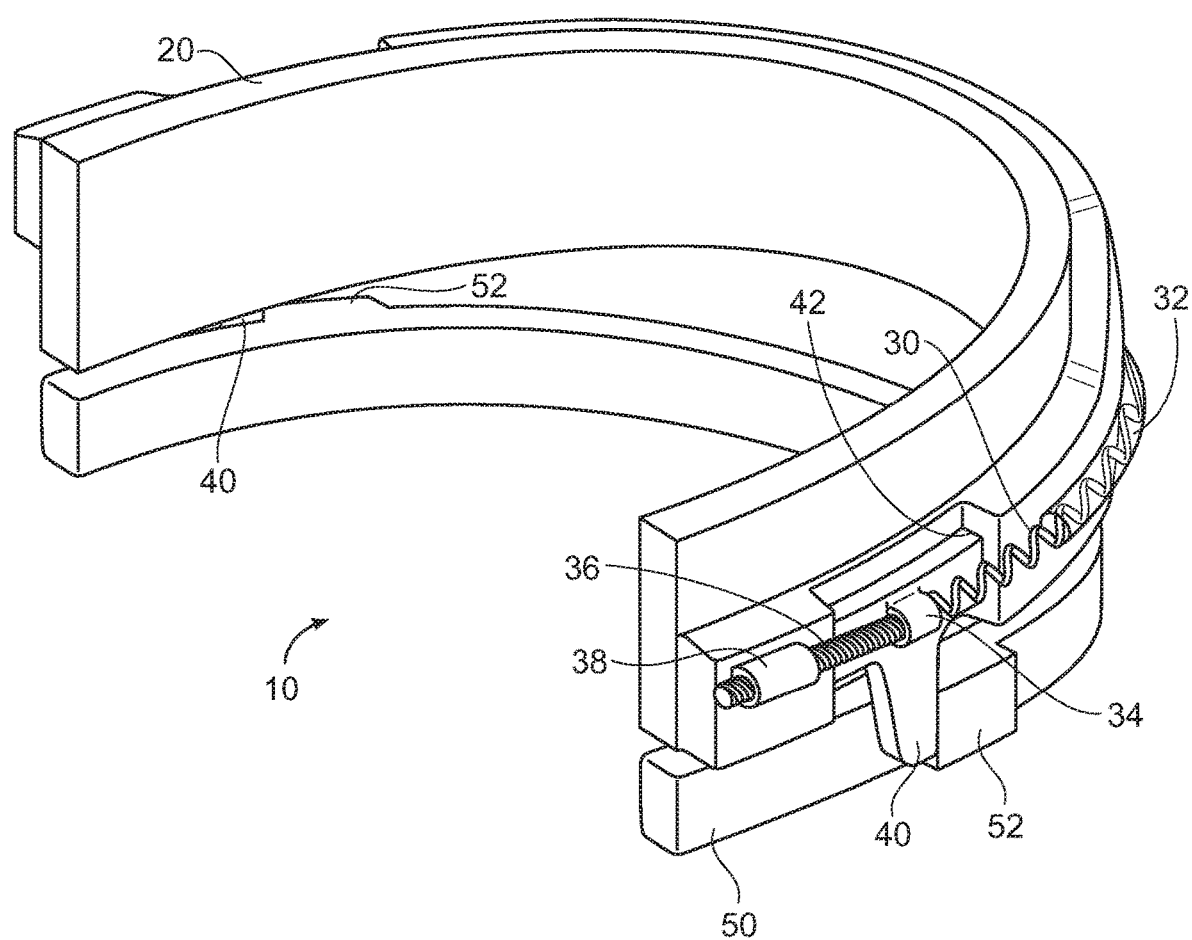
FIG. 12 is another rear perspective view of an apparatus for mandibular advancement of an oral appliance in accordance with an example embodiment.
Figure 13:
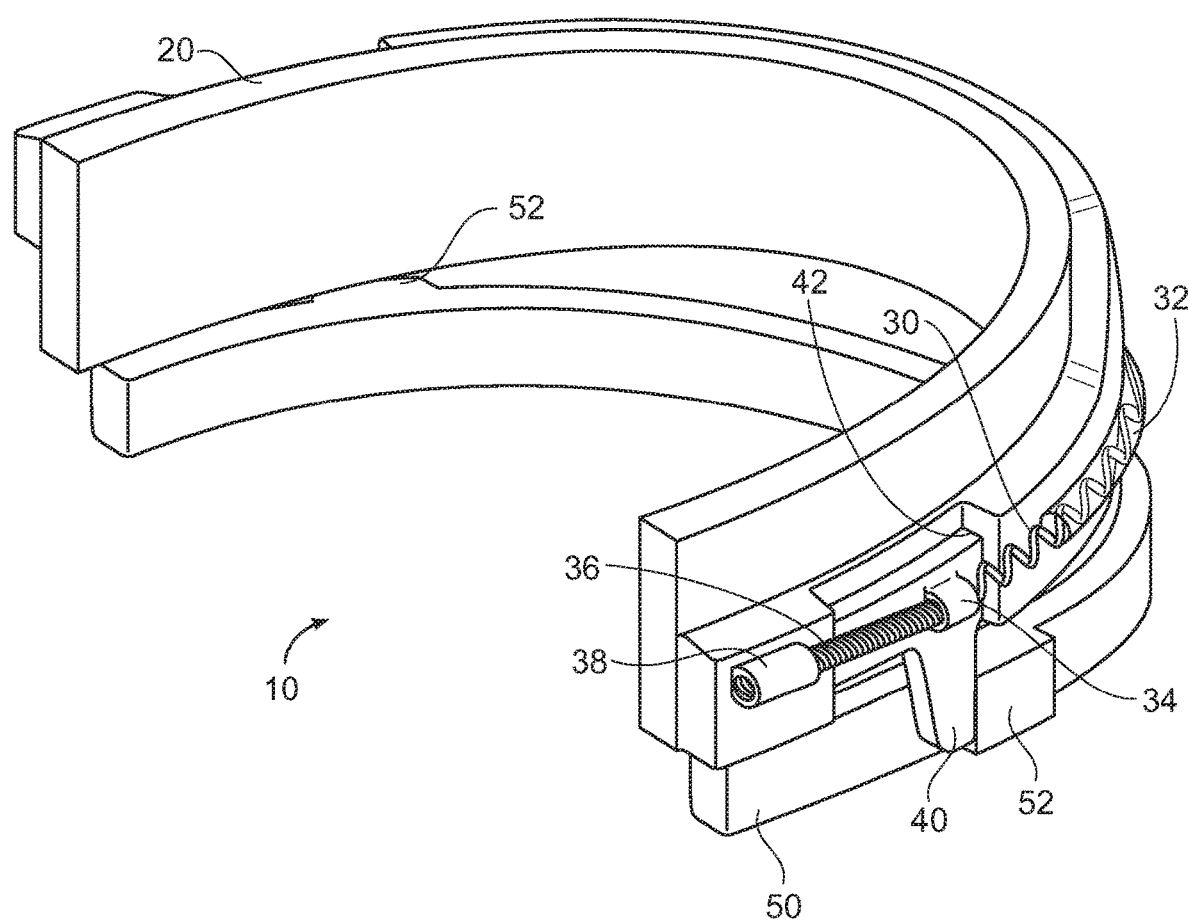
FIG. 13 is another rear perspective view of an apparatus for mandibular advancement of an oral appliance in accordance with an example embodiment.
Figure 15:
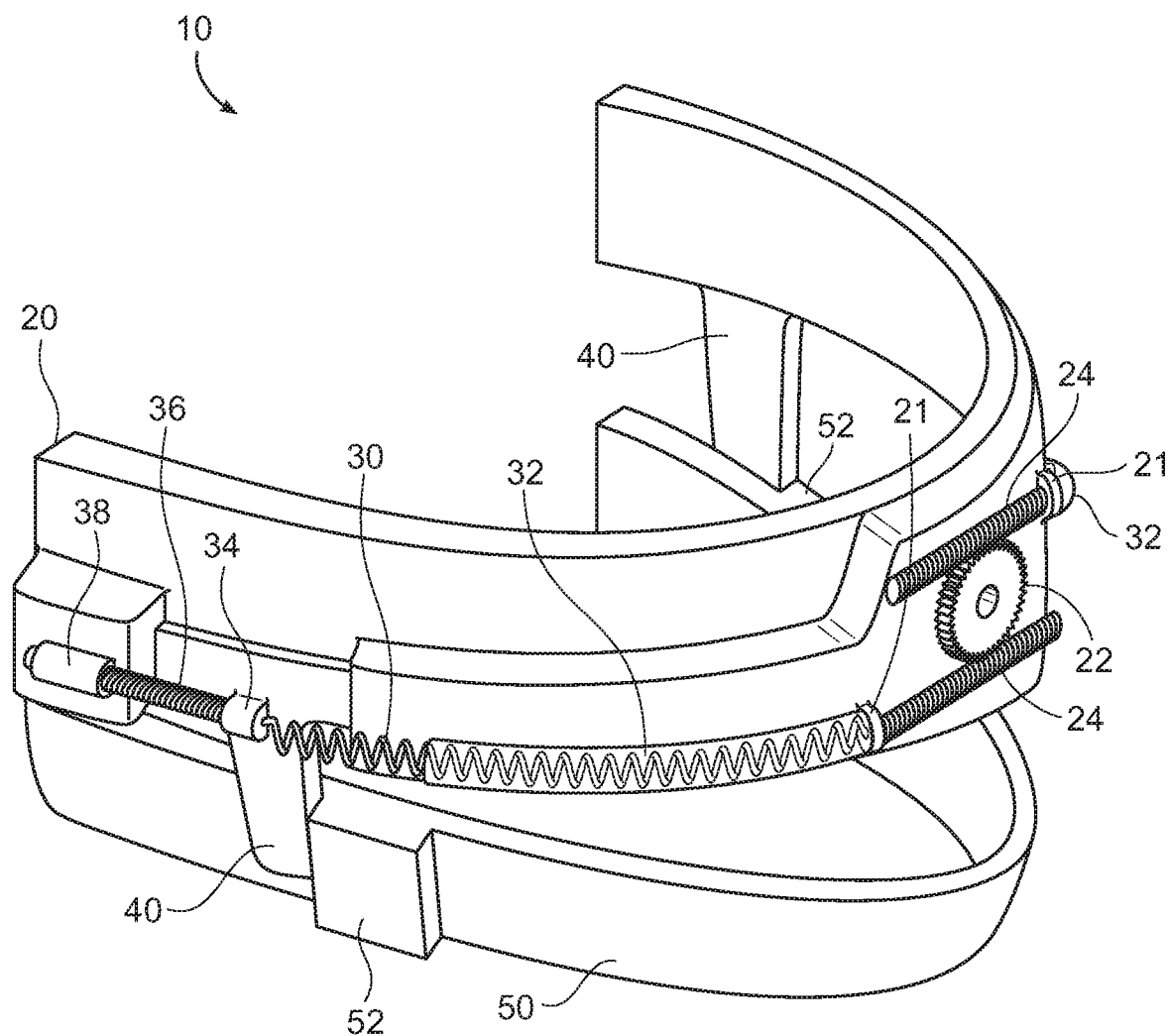
FIG. 15 is another front perspective view of an apparatus for mandibular advancement of an oral appliance in accordance with an example embodiment.

If the appliance is actuated in the other direction, the flanges 40 will move forward, both by a substantially equal amount. As an example, FIGS. 8 and 11 illustrate the appliance with the mandibular portion 50 in its most rearward position. Actuation of the drive gear 22 in a direction that will move the mandibular portion 50 forward will result in flange 40 pushing flange engaging member 52, and thus mandibular portion 50, forward, as shown in FIGS. 6, 7, 9 and 12, which represents a middle position of portion 50. FIGS. 10, 13 and 15 show the appliance with the mandibular portion 50 advanced as far as possible relative to the maxillary portion 20.

The helical members 30 also flex along their length as the actuator screws 30 move forward and back to advance or retract the mandibular portion 50 of the appliance 10. When the drive gear 22 is rotated, each worm screw 24 rotates by about the same amount, in opposite directions. To account for this, the actuator screws 36 on either side of the appliance 10 may have reverse threads from each other, so that clockwise rotation on one side, and counter-clockwise rotation on the other side of the appliance 10 results in forward (or reverse) linear displacement of each flange 40, one on each side of the appliance. The helical members 30 transfer the rotation of the worm screws 24 at the front of the appliance 10 to the actuator screws 36 at the rear portion of the appliance 10, the helical members 30 being rotationally coupled to both the worm screws 24 and the actuator screws 36.

In some example embodiments, actuation and adjustment of the appliance, comprising the drive gear 22, helical members 30, actuating screws 36, fixed nuts 38, may comprise a means for linearly displacing the first flange 40 and the second flange 40 in response to a rotational input.

In a method of using the oral appliance, rotating the drive gear 22 results in the first flange 40, the second flange 40, or both of them, being linearly displaced, and the displacement may be in substantially equal amounts due to adjustment of the single drive gear 22. As an example, rotation of the drive gear 22 provides for a single input point or action that results in the mandibular portion 50 of the appliance being advanced or moved forward relative to the upper, maxillary portion 20 of the appliance. This direction can of course also be reversed by driving gear 22 in the opposite direction.

Unless otherwise defined, all technical and scientific terms used herein have the same meaning as commonly understood by one of ordinary skill in the art to which this invention belongs. Although methods and materials similar to or equivalent to those described herein can be used in the practice or testing of the apparatus for mandibular advancement of an oral appliance, suitable methods and materials are described above. All publications, patent applications, patents, and other references mentioned herein are incorporated by reference in their entirety to the extent allowed by applicable law and regulations. The apparatus for mandibular advancement of an oral appliance may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

What is claimed is:

1. An adjustable oral appliance, comprising:
a first appliance portion comprising a gear assembly having a drive gear, wherein rotation of the drive gear rotates a worm screw that is rotatably coupled to a helical member that extends in an arc from a front position to a rear position of the first appliance portion;
a fixed nut secured proximate the rear position of the first appliance portion;
an actuator screw having a first end threadably engaged in the fixed nut and a second end rotatably coupled to the helical member such that the actuator screw rotates when the helical member rotates;
a first link slidably coupled to the first appliance portion, the first link also being coupled to the actuator screw proximate the second end so that rotation of the actuator screw causes a linear displacement of the first link relative to the first appliance portion as the actuator screw rotates within the fixed nut;
a second appliance portion having a first link-engaging member, wherein the first link exerts a force on the first link-engaging member when it is linearly displaced, and wherein the force causes the second appliance portion to be displaced relative to the first appliance portion;
a second helical member that extends in an arc from a front position to a rear position of the first appliance portion, wherein rotation of the drive gear rotates a second worm screw that is rotatably coupled to the second helical member;
a second fixed nut secured proximate the rear position of the first appliance portion;
a second actuator screw having a first end threadably engaged in the second fixed nut and a second end rotatably coupled to the second helical member;
a second link slidably coupled to the first appliance portion, the second link also being coupled to the second actuator screw proximate the second end so that rotation of the second actuator screw causes a linear displacement of the second link relative to the first appliance portion as the second actuator screw rotates within the second fixed nut; and
a second link-engaging member on the second appliance portion, wherein the linear displacement of the second link exerts a second force on the second link-engaging member when it is linearly displaced, and wherein the second force causes the second appliance portion to be displaced relative to the first appliance portion.

2. The adjustable oral appliance of claim 1, wherein the drive gear comprises a worm wheel and wherein the first link comprises a flange.

3. The adjustable oral appliance of claim 1, wherein the first appliance portion comprises a maxillary portion and the second appliance portion comprises a mandibular portion.

4. The adjustable oral appliance of claim 1, wherein the first appliance portion comprises a mandibular portion and the second appliance portion comprises a maxillary portion.

5. A method of using the adjustable oral appliance of claim 1, comprising:
rotating the drive gear such that the first link is linearly displaced.

6. The method of claim 5, wherein the first appliance portion comprises a maxillary portion and the second appliance portion comprises a mandibular portion.

7. A method of using the adjustable oral appliance of claim 1, comprising:
rotating the drive gear such that the first link and the second link are both linearly displaced.

8. The method of using the oral appliance of claim 7, wherein the first link and the second link are displaced in substantially equal amounts when the drive gear is rotated.

9. The adjustable oral appliance of claim 1, wherein the drive gear comprises a worm wheel and wherein the first link comprises a flange and wherein the second link comprises a flange.

10. The adjustable oral appliance of claim 1, wherein the first appliance portion comprises a maxillary portion and the second appliance portion comprises a mandibular portion.

11. The adjustable oral appliance of claim 1, wherein the first appliance portion comprises a mandibular portion and the second appliance portion comprises a maxillary portion.

12. The adjustable oral appliance of claim 10, wherein the drive gear comprises a single worm wheel, and wherein the first link and the second link are linearly displaced in substantially equal amounts in response to rotation of the drive gear.

13. An adjustable oral appliance, comprising:
a first appliance portion;
a first link slidably coupled to the first appliance portion at a first side;
a first means for linearly displacing the first link in response to a single rotational input;
a second appliance portion having a first link-engaging member, wherein the first link exerts a force on the first link-engaging member when it is linearly displaced relative to the first appliance portion, and wherein the force causes the second appliance portion to be displaced relative to the first appliance portion;
a second link slidably coupled to the first appliance portion at a second side;
a second means for linearly displacing the second link in response to the single rotational input; and
a second link-engaging member on the second appliance portion, wherein a linear displacement of the second link exerts a second force on the second link-engaging member when it is linearly displaced, and wherein the second force causes the second appliance portion to be displaced relative to the first appliance portion.

14. The adjustable oral appliance of claim 13, wherein the first link and the second link are linearly displaced in substantially equal amounts in response to the single rotational input.

15. A method of using the adjustable oral appliance of claim 13, comprising:
providing the single rotational input such that the first link and the second link are both linearly displaced.

16. The method of using the adjustable oral appliance of claim 15, wherein the first link and the second link are displaced in substantially equal amounts.

17. A method of using the adjustable oral appliance of claim 13, comprising:
providing the single rotational input such that the first link is linearly displaced.

* * * * *